(12) United States Patent
Morrissette et al.

(10) Patent No.: US 10,849,657 B2
(45) Date of Patent: Dec. 1, 2020

(54) SURGICAL INSTRUMENT GUIDE WITH INSUFFLATION CHANNELS

(71) Applicant: Intuitive Surgical Operations, Inc., Sunnyvale, CA (US)

(72) Inventors: Tyler J. Morrissette, Niantic, CT (US); Michael Ikeda, Saratoga, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 57 days.

(21) Appl. No.: 16/317,400

(22) PCT Filed: Jul. 12, 2017

(86) PCT No.: PCT/US2017/041787
§ 371 (c)(1),
(2) Date: Jan. 11, 2019

(87) PCT Pub. No.: WO2018/013734
PCT Pub. Date: Jan. 18, 2018

(65) Prior Publication Data
US 2019/0223911 A1    Jul. 25, 2019

Related U.S. Application Data

(60) Provisional application No. 62/361,931, filed on Jul. 13, 2016.

(51) Int. Cl.
*A61B 17/34* (2006.01)
*A61B 17/02* (2006.01)
(Continued)

(52) U.S. Cl.
CPC ............ *A61B 17/3474* (2013.01); *A61B 1/04* (2013.01); *A61B 17/0218* (2013.01);
(Continued)

(58) Field of Classification Search
CPC .................. A61B 17/3474; A61B 17/0218
See application file for complete search history.

(56) References Cited

U.S. PATENT DOCUMENTS 5,549,565 A * 8/1996 Ryan .................. A61B 17/3496
137/849
5,643,301 A * 7/1997 Mollenauer ........ A61B 17/3498
606/167

(Continued)

FOREIGN PATENT DOCUMENTS

| CN | 105534576 A | 5/2016 |
| WO | WO-2011100125 A1 | 8/2011 |
| WO | WO-2014144771 A1 | 9/2014 |

OTHER PUBLICATIONS

International Search Report and Written Opinion for Application No. PCT/US2017/041787, dated Oct. 25, 2017, 12 pages.

(Continued)

*Primary Examiner* — Christian A Sevilla
(74) *Attorney, Agent, or Firm* — Schwegman Lundberg & Woessner, P.A.

(57) ABSTRACT

A cannula and instrument guide assembly includes a cannula with a proximal portion and a tube. An instrument guide is removably inserted into the proximal portion of the cannula and extends through the cannula to a distal end of the tube. The proximal portion of the cannula has an insufflation port. The instrument guide provides at least one interior passageway to support a shaft of a surgical instrument that passes through the instrument guide. One or more channels on an outer surface of the instrument guide provide a passage for insufflation gas received from the insufflation port to the distal end of the tube. The one or more channels have a first cross-sectional area at a proximal end and a second, larger cross-sectional area at a distal end. The one or more channels may have the first cross-sectional area along a majority of the length of the channels.

18 Claims, 2 Drawing Sheets

(51) Int. Cl.
*A61B 34/35* (2016.01)
*A61B 1/04* (2006.01)
*A61M 39/06* (2006.01)
*A61B 34/37* (2016.01)
*A61M 13/00* (2006.01)

(52) U.S. Cl.
CPC .......... *A61B 17/3421* (2013.01); *A61B 34/35* (2016.02); *A61B 34/37* (2016.02); *A61M 13/003* (2013.01); *A61M 39/06* (2013.01); *A61B 2017/3445* (2013.01); *A61M 2039/0646* (2013.01)

(56) References Cited

U.S. PATENT DOCUMENTS

| | | | |
|---|---|---|---|
| 5,707,351 A | * | 1/1998 | Dorsey, III ......... A61M 1/0062 604/30 |
| 2005/0077689 A1 | * | 4/2005 | Hueil .................. A61B 17/3421 277/628 |
| 2008/0242930 A1 | * | 10/2008 | Hanypsiak ......... A61B 17/3421 600/114 |
| 2009/0318866 A1 | | 12/2009 | Ferrari |
| 2010/0004599 A1 | | 1/2010 | Zhou et al. |
| 2010/0228094 A1 | * | 9/2010 | Ortiz .................. A61B 17/0293 600/205 |
| 2011/0087159 A1 | * | 4/2011 | Parihar .................. A61B 17/34 604/26 |
| 2013/0237902 A1 | | 9/2013 | McGinley et al. |
| 2014/0276947 A1 | | 9/2014 | Lambrecht et al. |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

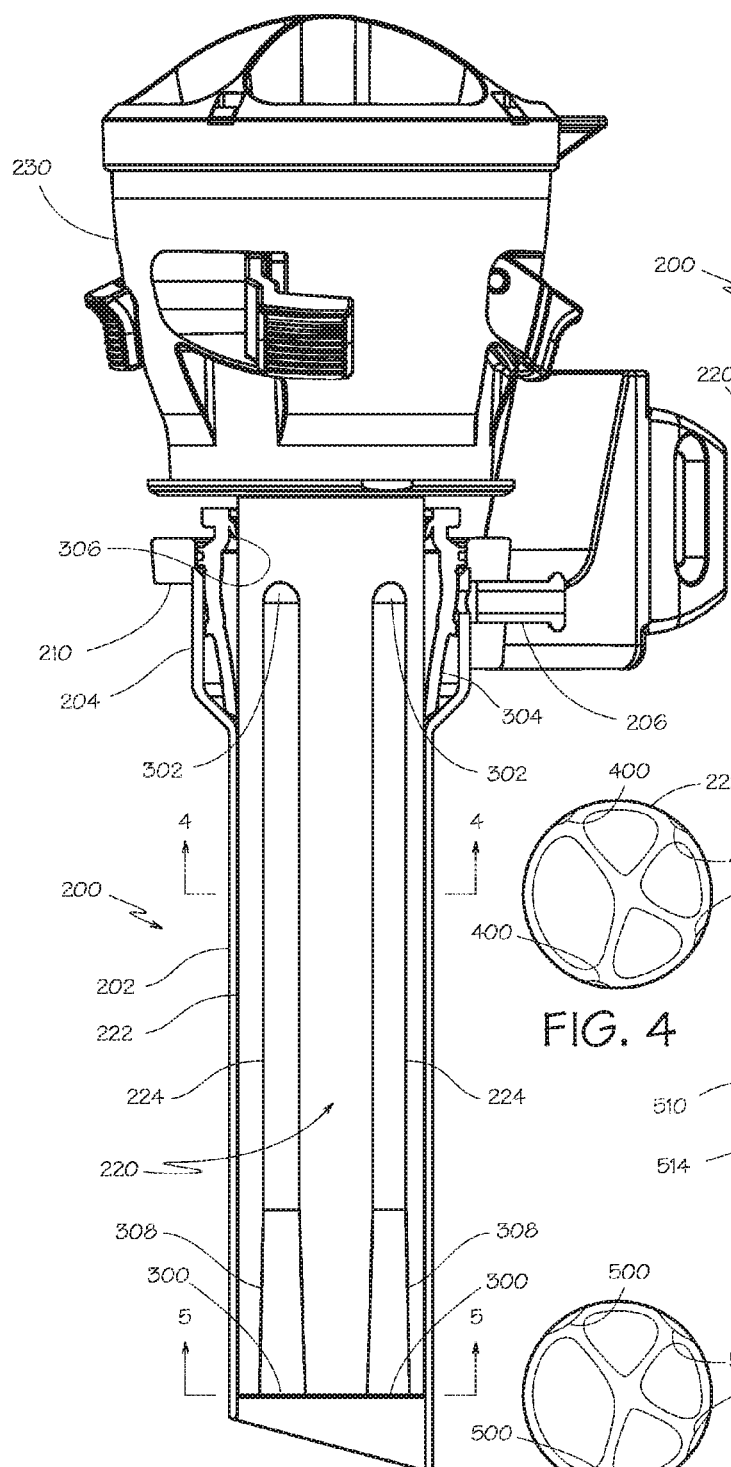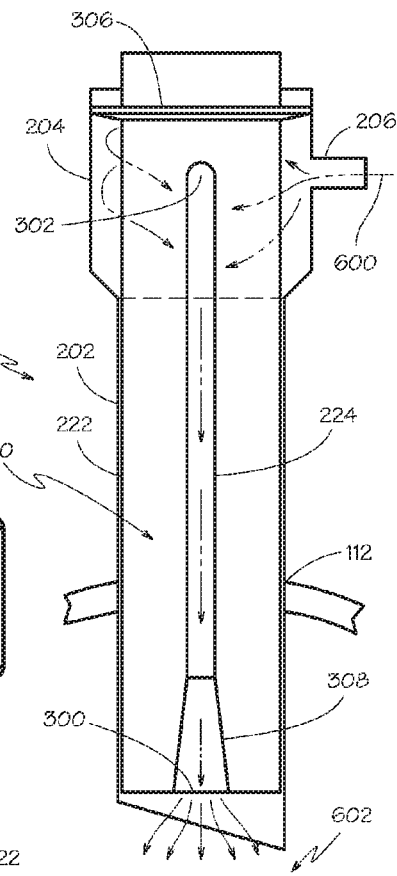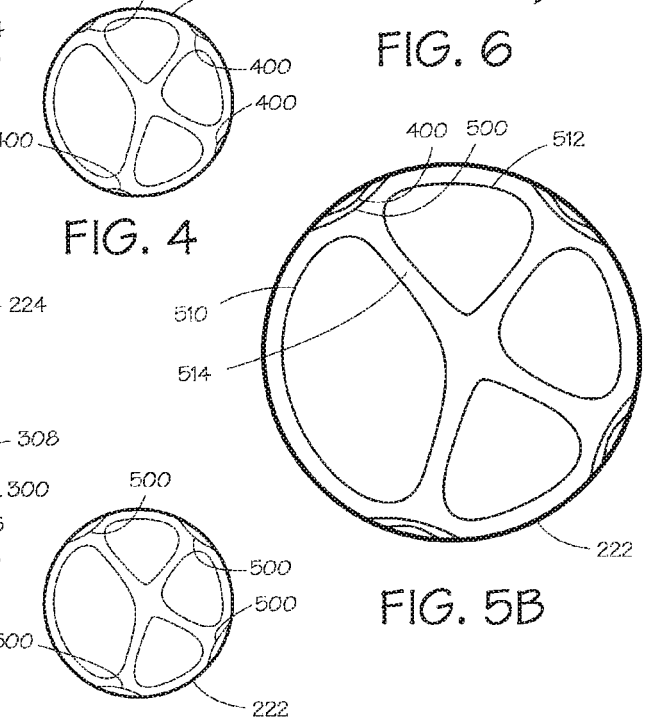

SURGICAL INSTRUMENT GUIDE WITH INSUFFLATION CHANNELS

CROSS REFERENCE TO RELATED APPLICATIONS

This application is a National Stage Filing under 35 U.S.C. 371 from International Application No. PCT/US2017/041787, filed on 12 Jul. 2017, and published as WO 2018/013734 A1 on 18 Jan. 2018,which claims the benefit pursuant to 35 U.S.C. 119(e) of U.S. Provisional Application No. 62/361,931, filed 13 Jul. 2016, each of which application is specifically incorporated herein, in its entirety, by reference.

BACKGROUND

Field

Embodiments of the invention relate to the field of endoscopic surgical instruments and, in particular, to instrument guides for endoscopic surgical instruments that include channels for introducing insufflation gases.

Background

Minimally invasive medical techniques have been used to reduce the amount of extraneous tissue which may be damaged during diagnostic or surgical procedures, thereby reducing patient recovery time, discomfort, and deleterious side effects. Traditional forms of minimally invasive surgery include endoscopy. One of the more common forms of endoscopy is laparoscopy, which is minimally invasive inspection or surgery within the abdominal cavity. In traditional laparoscopic surgery, a patient's abdominal cavity is insufflated with gas, and cannula sleeves are passed through small (approximately 12 mm) incisions in the musculature of the patient's abdomen to provide entry ports through which laparoscopic surgical instruments can be passed in a sealed fashion.

The laparoscopic surgical instruments generally include a laparoscope for viewing the surgical field and surgical instruments having end effectors. Typical surgical tools include clamps, graspers, scissors, staplers, and needle holders, for example. The surgical instruments are similar to those used in conventional (open) surgery, except that the end effector of each surgical instrument is separated from its handle by an approximately 30 cm. long extension tube, for example, so as to permit the operator to introduce the end effector to the surgical site and to control movement of the end effector relative to the surgical site from outside a patient's body.

To reduce the trauma of minimally invasive surgery even further, techniques are being developed to allow minimally invasive surgery using only a single access port into the body, such as a single incision or single natural body orifice. This access may be accomplished by using a somewhat larger cannula that can accommodate all of the instruments required for the surgery. Minimally invasive surgery performed through a single incision or natural orifice may be referred to as single port access (SPA) surgery. The single cannula that provides the single port may be introduced through a body orifice or through an incision.

If multiple surgical instruments and/or camera instruments are introduced to a surgical site through a single cannula, it is desirable to use as small a cannula as possible, consistent with the size of the instruments to be passed through the cannula. Passages also must be provided to supply insufflation gas to inflate the surgical site and to continually replace gas lost to leakage. The passages also may also allow the surgical site to be evacuated.

Therefore, there is a need for better and more effective devices for introducing surgical instruments and supplying insufflation gas to a surgical site through a small incision.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements:

FIG. 3 is a side view of assembled access port with a portion of the cannula cut away to show the instrument guide that is inserted into the cannula.

FIG. 4 is a cross-section of the instrument guide taken along line 4-4 in FIG. 3.

FIG. 5A is a cross-section of the instrument guide taken along line 5-5 in FIG. 3.

FIG. 5B is an enlarged cross-section of the instrument guide taken along line 5-5 in FIG. 3.

FIG. 6 is a schematic side view of the instrument guide inserted into the cannula to illustrate the flow of insufflation gas.

DESCRIPTION OF EMBODIMENTS

Figure 1:
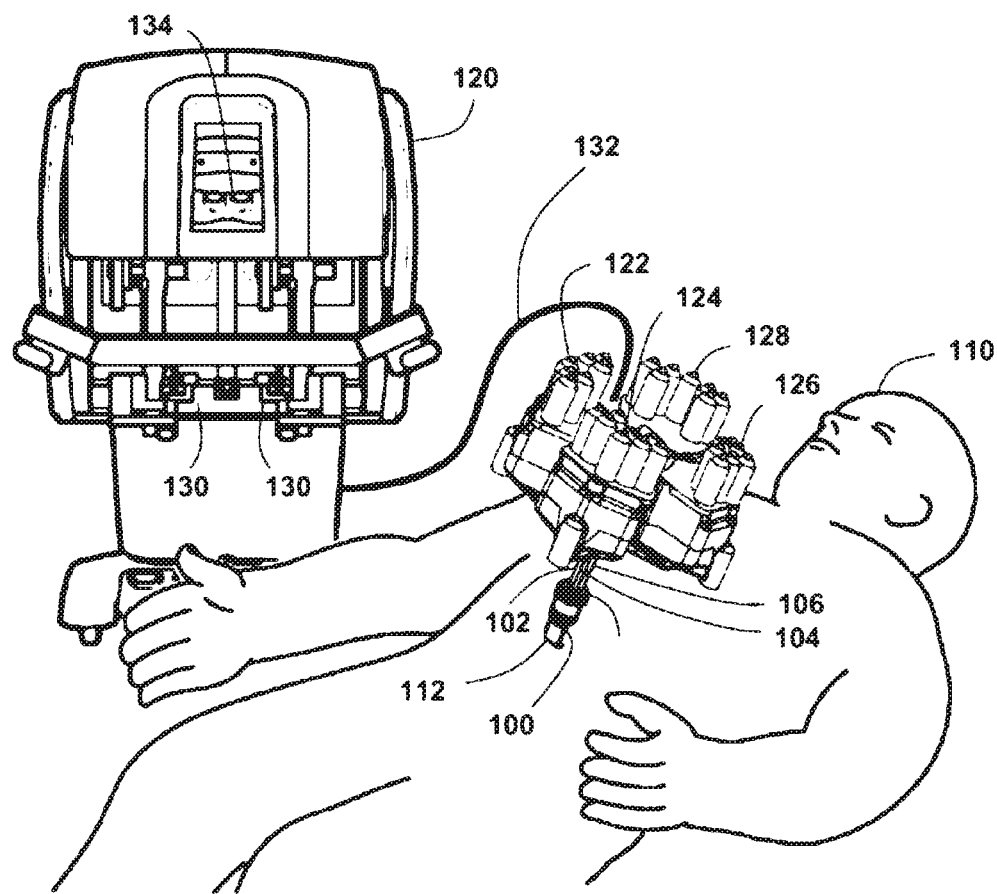
FIG. 1 is a view of an illustrative teleoperated surgical system.

In the following description, numerous specific details are set forth. However, it is understood that embodiments of the invention may be practiced without these specific details. In other instances, well-known circuits, structures, and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a," "an," and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The term "object" generally refers to a component or group of components. For example, an object may refer to either a pocket or a boss of a disk within the specification or claims. Throughout the specification and claims, the terms "object," "component," "portion," "part" and "piece" are used interchangeably.

The terms "or" and "and/or" as used herein are to be interpreted as inclusive or meaning any one or any combination. Therefore, "A, B, or C" or "A, B, and/or C" mean "any of the following: A; B; C; A and B; A and C; B and C; A, B, and C." An exception to this definition will occur only when a combination of elements, functions, steps, or acts are in some way inherently mutually exclusive.

Terms of approximation, such as "substantially" and "about," as used herein are to be interpreted as meaning equal to a stated amount within a tolerance that is appropriate to the manufacturing processes that produces the stated amount or to the use or requirement for the stated amount. Thus a length that is substantially a stated amount could be the stated amount plus or minus a small amount if the length is produced by a precise process or represents a critical dimension. Conversely, a length that is substantially a stated amount could be the stated amount plus or minus a large amount if the length is produced by an imprecise process or represents a non-critical dimension.

The terms "instrument" and "surgical instrument" are used herein to describe a medical device configured to be inserted into a patient's body and used to carry out surgical or diagnostic procedures. The surgical instrument typically includes an end effector associated with one or more surgical tasks, such as a forceps, a needle driver, a shears, a bipolar cauterizer, a tissue stabilizer or retractor, a clip applier, an anastomosis device, an imaging device (e.g., an endoscope or ultrasound probe), and the like. Some instruments used with embodiments of the invention further provide an articulated support (sometimes referred to as a "wrist") for the surgical tool so that the position and orientation of the surgical tool can be manipulated with one or more mechanical degrees of freedom in relation to the instrument's shaft. Further, many surgical end effectors include a functional mechanical degree of freedom, such as jaws that open or close, or a knife that translates along a path. Surgical instruments may also contain stored (e.g., on a semiconductor memory inside the instrument) information that may be permanent or may be updatable by the surgical system. Accordingly, the system may provide for either one-way or two-way information communication between the instrument and one or more system components.

FIG. 1 shows a pictorial view of a minimally invasive teleoperated surgical procedure on a patient 110 using a single access port 100 for teleoperated surgical instruments 102, 104, 106. The single access port 100 is inserted through a single incision 112. Typically three or four surgical instruments (instruments 102, 104, and 106 are illustrated), including a camera instrument, are introduced through the single access port 100. In addition, there will generally be provisions for introducing an insufflation gas, such as carbon dioxide ($CO_2$), at or near the single access port 100. It will be appreciated that single port surgery uses a substantial amount of equipment located in a small amount of space.

The teleoperated surgical instruments 102, 104, and 106, which may include a camera instrument that may provide images of the surgical site and other instruments at the surgical site, are each coupled to a corresponding actuator, such as one of actuators 122, 124, 126, and 128. The actuators 122, 124, 126, and 128 are servo actuators that allow a surgeon to manipulate the surgical instruments using a computer-mediated control station 120. These manipulations may include functions such as changing the position and orientation of the surgical instrument's end effector (to include a camera) and operating the end effector (such as closing jaws to effect grasping, cutting, etc.). Such actuator control of surgical instruments may be referred to by various terms, such as teleoperated surgery. The actuators 122, 124, 126, and 128 may be supported on a separate structural arm that, once positioned, can be fixed relative to the patient 110. In various implementations the supporting arm may be manually positioned, may be positioned by the surgeon, or may be automatically positioned by the system as the surgeon moves one or more of the surgical instruments.

A control system couples a computer-mediated control station 120 to the teleoperated actuators 122, 124, 126, and 128. Here "computer" broadly encompasses a data processing unit that incorporates a memory and an additive or logical function, such as an arithmetic logic unit, that is programmable to perform arithmetic or logical operations. The control system may coordinate movement of the input devices with the movement of their associated surgical instruments so that the images of the surgical instruments 102, 104, 106, as displayed to the surgeon, appear at least substantially connected to the input devices in the hands of the surgeon. Further levels of connection will also often be provided to enhance the surgeon's dexterity and ease of use of the surgical instruments 102, 104, and 106.

The computer-mediated control station 120 may provide hand operated master controllers 130 that allow manipulation of the teleoperated surgical instruments 102, 104, 106 by transmitting signals, such as electrical or optical control signals provided by cables 132, to the actuators 122, 124, 126, and 128 that control the actions of the coupled surgical instruments 102, 104, and 106. Typically one of the surgical instruments, surgical instrument 102 for example, will be a camera instrument that is manipulated to place the remaining surgical instruments and the objects being manipulated within a field of view of the camera. The camera instrument transmits signals to the control station 120 so that an image captured by the camera of the instruments and objects within the field of view can be displayed on a visual display 134 that is viewed by the surgeon as the coupled surgical instruments 104, 106 are manipulated. The hand-operated controllers 130 and the visual display 134 may be arranged to provide an intuitive control of the surgical instruments 104, 106, in which the instruments move in a manner similar to the operator's hand movements with the controllers.

Figure 2:
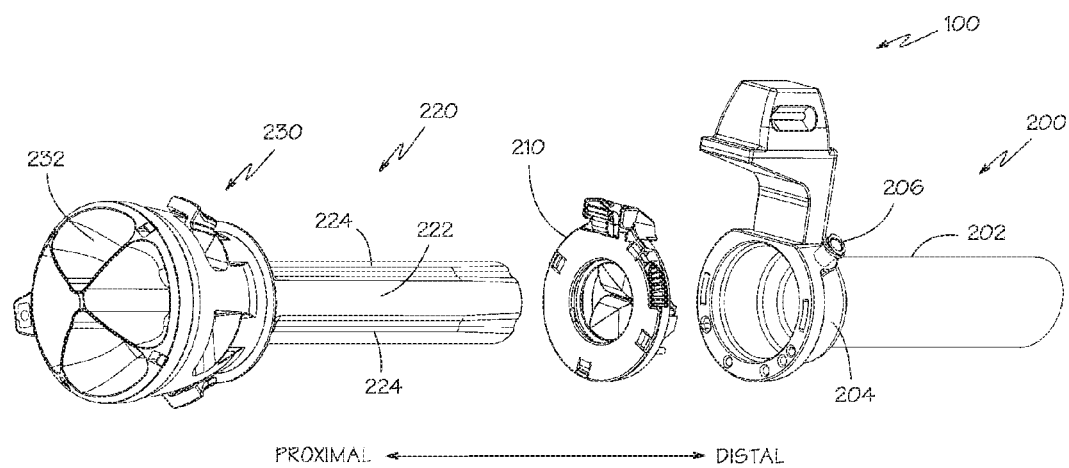
FIG. 2 is a pictorial view of an unassembled access port.

FIG. 2 is a pictorial view of an unassembled cannula and instrument guide assembly that forms an access port 100 which can be inserted through the incision 112. The access port 100 is shown before the parts are assembled into the configuration used during a surgical procedure. When assembled, the cannula and instrument guide assembly provides the single port access shown in FIG. 1.

The access port 100 includes a cannula 200 having a lumen or tube 202 that is inserted through the incision 112 to separate and protect the incision. The access port 100 further includes an instrument guide 220 that is inserted into the cannula 200. The instrument guide 220 may be coupled to the cannula 200 in various ways to retain the instrument guide in the cannula during the surgical procedure. The instrument guide 220 guides one or more instruments through the cannula 200 to facilitate instrument access to the surgical site.

The cannula 200 includes a proximal portion 204 having an insufflation port 206 and a tube 202 coupled to the proximal portion. The insufflation port 206 receives an insufflation gas, such as carbon dioxide ($CO_2$), that is introduced to the surgical site through the tube 202 portion of the cannula 200.

The access port 100 may include a seal assembly 210 that is coupled to the cannula 200. The seal assembly 210 seals the access port 100 to reduce loss of insufflation gas when the instrument guide 220 is not inserted into the cannula 200.

The instrument guide 220 may be joined to a funnel assembly 230 that provides instrument receivers 232 to guide instruments into passages in the instrument guide at the proximal end of the instrument guide. The funnel assembly 230 may include seals that seal the instrument passages in the instrument guide 220 to reduce loss of insufflation gas when an instrument is not inserted into an instrument passage. The instrument guide 220 may include one or more instrument passages. Instrument guides may include one, two, three, four, five, six, or more instrument passages. The instrument passages may all be the same size and shape or they may vary in size and/or shape. Each instrument passage may have a circular cross-section or an oval cross-section or other cross-section shape that corresponds to the shape of the instrument shaft to be supported by the instrument passage.

The distal portion of the instrument guide 220 is configured to fit closely within the tube 202 portion of the cannula 200. Each of the one or more instrument passages in the instrument guide 220 is configured to support a single surgical instrument at a defined position within the cannula 200. The surgical instruments are inserted into the access port 100 through the instrument receivers 232 in the funnel assembly 230 so that they are directed into the instrument passages at a proximal end of the instrument guide 220. The surgical instruments are supported by the instrument passages until they emerge from a distal end of the instrument guide 220. In some embodiments, the instrument guide 220 may be formed from an electrically non-conductive material to aid in electrically isolating the instruments, which may carry an electrical charge used for electrosurgical applications (e.g., cauterization). In other embodiments, the instrument guide 220 may be formed from a conductive material, such as metal or conductive plastic, to aid in dissipating any electrical charge that might build up on the instruments passing through the guide.

In some embodiments, the cannula 200 may be reusable (e.g., after cleaning and sterilization). Some or all of the instrument guide 220, the funnel assembly 230, and the seal assembly 210 may be provided as a sterile, disposable kit, e.g., a gamma sterilized kit, so that a new instrument guide, a new funnel assembly, and/or a new seal assembly may be used for each surgical procedure.

FIG. 3 shows a side view of the access port 100 with the cannula 200 cut away along a diameter to show the instrument guide 220 inserted into the cannula. The instrument guide 220 includes at least one channel 224 on an outer surface 222 of an outer wall of the instrument guide to form a passage for insufflation gas from the insufflation port 206 to the distal end of the tube 202 portion of the cannula 200.

The channel 224 is adjacent an interior surface of the tube 202 to form the passage for insufflation gas when the instrument guide 220 is inserted into the tube. The channel 224 extends completely to the distal end 300 of the instrument guide 220. The channel 224 extends toward but does not reach the proximal end of the instrument guide 220. The channel 224 extends toward the proximal end sufficiently for the proximal end 302 of the channel to receive insufflation gas that flows from the insufflation port 206 and through the proximal portion 204 of the cannula 200.

The seal assembly 210 may include a proximal seal 306 and sealing flaps 304. The proximal seal 306 seals the instrument guide 220 beyond the proximal end 302 of the channels 224 to prevent insufflation gas from escaping past the instrument guide at the proximal end of the cannula 200. The sealing flaps 304 are opened when the instrument guide 220 is inserted into the tube 202. While the sealing flaps 304 appear to block the flow of insufflation gas from the insufflation port 206 to the proximal end 302 of the channels, there are openings between the flaps that allow the flow of insufflation gas throughout the proximal portion 204 of the cannula 200. Thus the cannula and instrument guide assembly of the access port 100 provides a mechanism for introducing insufflation gas into the surgical sites while minimizing the loss of insufflation gas from the assembly.

FIG. 4 is a cross-section of the instrument guide 220 taken along section line 4-4. FIGS. 5A and 5B are cross-sections of the instrument guide 220 taken along section line 5-5. FIG. 5A omits the detail of the channel end view that is shown in the enlarged view of FIG. 5B.

It is necessary to provide a flow rate of insufflation gas sufficient to inflate the surgical region to a set pressure, perhaps 8 to 14 mm Hg, and replace gas loss due to leakage. Insufflation gas may be supplied at a pressure of about 15 mm Hg (about 2,000 Pa). The flow rate may be about 20 l/min. It will be appreciated that the velocity of insufflation gas flowing through the one or more channels 224 depends on the cross-sectional area of the channel. The flow will have a higher velocity when the cross-sectional area is small and a lower velocity when the cross-sectional area is large. But it is desirable to have a small cross-sectional area for the one or more channels 224 to minimize the diameter of the instrument guide 220 and the cannula's tube 202. The cross-sectional area for the one or more channels 224 is constrained by the need to maintain a certain wall thickness for the structural integrity and manufacturability of the instrument guide 220.

It is also desirable to avoid high velocity flow of insufflation gas that can disturb or even damage tissues adjacent the distal end of the cannula 200 where the insufflation gas is discharged into the surgical site. To provide a small diameter instrument guide 220 while minimizing the discharge velocity of insufflation gas, the one or more channels 224 having a first cross-sectional area at a proximal end of the channel and a second cross-sectional area at a distal end of the channel that is larger than the first cross-sectional area.

The one or more channels 224 have the first cross-sectional area for the majority of the length of the channel. A transitional section 308 begins close to the distal end of the channel 224 to provide a transition to the second cross-sectional area. The transition is made just long enough to avoid introducing turbulence in the flow of the insufflation gas. In some embodiments, the transition from the first cross-sectional area to the second cross-sectional area is about 1 inch (25 mm) long. By limiting the larger cross-sectional areas to the distal end 300 of the instrument guide 220, the adverse consequences of the larger cross-sectional areas are minimized. This allows the instrument guide 220 to have a smaller diameter than would be possible if the channel 224 had the second cross-sectional area for its entire length. In some embodiments, the second cross-sectional area is at least twice the first cross-sectional area, reducing the discharge velocity of the insufflation gas to half or less than the velocity at the proximal end of the channel. For example, in one embodiment the first cross-sectional area is about 0.0023 in² (1.5 mm²) and the second cross-sectional area is about 0.0050 in² (3.0 mm²).

The one or more channels 224 are located relative to the interior passageways to provide a first wall thickness for the instrument guide where the channel has the first cross-sectional area and a second wall thickness for the instrument guide where the at least one channel has the second cross-sectional area, the second wall thickness being less than the first wall thickness.

FIG. 6 shows a schematic side view of the instrument guide 220 inserted into the cannula 200 to illustrate the flow of insufflation gas from the insufflation port 206 to the surgical site 602. The double dashed arrows suggest the flow of insufflation gas 600. The cannula 200 is inserted through an incision 112 which seals against the outside of the cannula. The proximal portion 204 of the cannula 200 forms a plenum that supplies insufflation gas. The proximal portion 204 is sealed at the proximal end by the proximal seal 306 sealing against the instrument guide 220.

Insufflation gas enters the one or more channels 224 on the outer surface 222 of the instrument guide 220 from the plenum formed by the proximal portion 204 of the cannula 200 and flows toward the distal end 300 of the instrument guide. The one or more channels 224 include a transition section 308 that has an increasing cross-sectional area at the distal end 300 of the channels. As suggested by the reduced length of the double dashed arrow in the transition section 308, the increasing cross-sectional area of the transition section reduces the velocity of the insufflation gas before it is discharged into the surgical site 602.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. For example, while the use of the channels of the instrument guide have been described for the delivery of insufflation gas to the surgical site, the same or similar channels can be used to evacuate gases and/or smoke from the surgical site. The description is thus to be regarded as illustrative instead of limiting.

What is claimed is:

1. A medical device comprising:
an instrument guide having an outer wall, a distal end, an interior passageway, and an insufflation gas channel;
the outer wall extending to the distal end of the instrument guide;
the interior passageway being shaped to support a shaft of a surgical instrument inserted through the interior passageway; and
the insufflation gas channel being defined in an outer surface of the outer wall and extending to the distal end of the instrument guide, the insufflation gas channel having a first cross-sectional area at a position at which insufflation gas is introduced into the insufflation gas channel and a second cross-sectional area at the distal end of the instrument guide, the second cross-sectional area being larger than the first cross-sectional area.

2. The medical device of claim 1, wherein the insufflation gas channel has the first cross-sectional area along a majority of a length of the insufflation gas channel.

3. The medical device of claim 1, wherein the insufflation gas channel is located relative to the interior passageway to provide a first wall thickness for the outer wall of the instrument guide where the insufflation gas channel has the first cross-sectional area and a second wall thickness for the outer wall of the instrument guide where the insufflation gas channel has the second cross-sectional area, the second wall thickness being less than the first wall thickness.

4. The medical device of claim 1, wherein the insufflation gas channel extends toward, but does not reach, a proximal end of the instrument guide.

5. The medical device of claim 1, wherein the second cross-sectional area of the insufflation gas channel is at least twice the first cross-sectional area.

6. The medical device of claim 1, further comprising:
a cannula including a proximal portion, an insufflation port at the proximal portion of the cannula, and a tube coupled to the proximal portion of the cannula;
wherein the instrument guide is removably inserted into the proximal portion of the cannula and extends through the cannula to a distal end of the tube.

7. The medical device of claim 6, wherein the insufflation gas channel is adjacent an interior surface of the tube of the cannula to form a passage for insufflation gas.

8. The medical device of claim 1, wherein the instrument guide further comprises a funnel assembly coupled to a proximal portion of the instrument guide to reduce insufflation gas leakage from the proximal portion of the instrument guide and to guide insertion of the shaft of the surgical instrument into and through the interior passageway of the instrument guide.

9. The medical device of claim 1, wherein the instrument guide further comprises a plurality of interior passageways.

10. The medical device of claim 9, wherein the instrument guide further comprises a plurality of radial walls, each of the plurality of radial walls being between two of the plurality of interior passageways.

11. The medical device of claim 10, wherein the instrument guide further comprises a plurality of insufflation gas channels, each of the plurality of insufflation gas channels is further defined in the outer surface of the outer wall opposite a location where one of the plurality of radial walls joins the outer wall.

12. A method of providing insufflation gas to a surgical site, the method comprising:
inserting a cannula through an incision, the cannula including a proximal portion having an insufflation port, and a tube coupled to the proximal portion;
inserting an instrument guide into the proximal portion of the cannula and through the cannula to a distal end of the tube, the instrument guide providing an interior passageway to support a shaft of a surgical instrument, and an insufflation gas channel on an outer surface of the instrument guide to form a passage for insufflation gas from the insufflation port to the distal end of the tube, the insufflation gas channel having a first cross-sectional area at a proximal end of the insufflation gas channel and a second cross-sectional area at a distal end of the insufflation gas channel being larger than the first cross- sectional area; and
supplying insufflation gas to the insufflation port.

13. The method of providing insufflation gas of claim 12, wherein the insufflation gas channel is adjacent an interior surface of the tube to form the passage for insufflation gas.

14. The method of providing insufflation gas of claim 12, wherein the insufflation gas channel extends toward, but does not reach, a proximal end of the instrument guide.

15. The method of providing insufflation gas of claim 12, wherein the insufflation gas channel has the first cross-sectional area along a majority of a length of the insufflation gas channel.

16. The method of providing insufflation gas of claim 12, wherein the second cross-sectional area is at least twice the first cross-sectional area.

17. The method of providing insufflation gas of claim 12, further comprising coupling a funnel assembly to the proximal portion of the cannula to reduce insufflation gas leakage from the proximal portion of the cannula and to guide insertion of the shaft of the surgical instrument into and through the interior passageway of the instrument guide.

18. The method of providing insufflation gas of claim 12, wherein the insufflation gas channel is located relative to the interior passageway to provide a first wall thickness for the instrument guide where the insufflation gas channel has the first cross-sectional area and a second wall thickness for the instrument guide where the insufflation gas channel has the second cross-sectional area, the second wall thickness being less than the first wall thickness.

* * * * *